March 23, 1965 E. H. SCANLON Plant Pat. 2,489
PEAR TREE
Filed Dec. 27, 1963
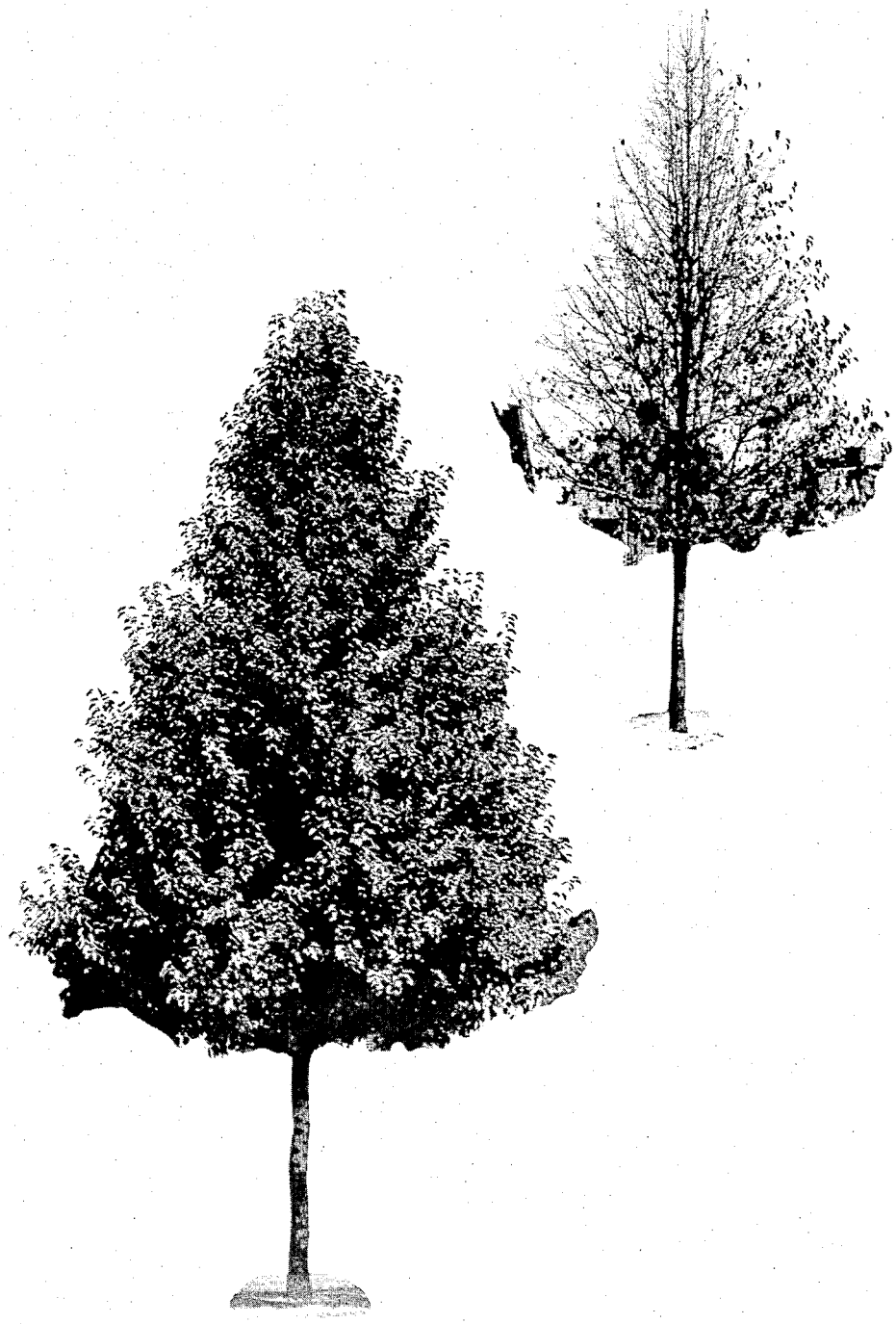
INVENTOR:
EDWARD H. SCANLON
By: Philip D. Gobrick
ATT'Y.

United States Patent Office

Plant Pat. 2,489
Patented Mar. 23, 1965

2,489
PEAR TREE

Edward H. Scanlon, 7621 Lewis Road,
Olmsted Falls, Ohio

Filed Dec. 27, 1963, Ser. No. 334,067
1 Claim. (Cl. Plt.—36)

The present invention or discovery relates to a new and distinct variety of pear tree and more particularly to a new and distinct variety of the pear tree species, *Pyrus calleryana.*

The pear tree variety which is the subject matter of this invention or discovery differs from the Callery pear species, *Pyrus calleryana,* primarily in its form, having a head which is compactly and definitely conical, in contrast with the species, where the shape is not uniform among individuals, and ranges from broadly conical to almost round, with a loose and open form. The new variety is of a distinctly excurrent type with the branches departing from the trunk at about a 40° angle and then turning upwardly; the branches becoming shorter toward the top of the tree.

This new variety is readily distinguished from *Pyrus calleryana* Bradford, in having spines, whereas the Bradford pear is non-spiny; and again by its shape in contrast with the Bradford pear having a broad ovate form and the loose, open form characteristic of most *Pyrus calleryana* seedlings.

The characteristic shape and form can be readily seen from the drawing, wherein:

FIG. 1 shows the new variety in foliage; and

FIG. 2 shows the specimen of FIG. 1 in dormant state with the branching character clearly apparent.

That it is a variety of the pear tree species, *Pyrus calleryana,* is evident from its community of characteristics in a standard botanical description of the species as follows:

Branchlets: Glabrous;

Winter buds: Finely pubescent;

Leaves: Broad-ovate to ovate, short acuminate, rounded or broad-cuneate at base; 4–8 cm. long, usually quite glabrous;

Petioles: 2–4 cm. long;

Flowers: 2–2½ cm. across;

Fruit: Globular, about 1 cm. across, slender-stalked, brown, dotted.

The new variety has been asexually reproduced by budding and by grafting on Callery pear understock at applicant's nursery in Olmstead Falls, Ohio, and also by budding at applicant's growing grounds in Oregon, and the distinguishing shape characteristic whereby the variety is distinguished from the species has been found to be transmitted to the clone.

The new variety was discovered as a cultivated seedling in an ornamental planting.

I claim:

A new and distinct variety of pear tree, of the species Callery pear, distinguished from the species by its compact and distinctly conical head shape, with branches departing from the trunk at an angle of about 40° and then turning upwardly and shortening as the branching approaches the top.

No references cited.

ABRAHAM G. STONE, *Primary Examiner.*